(12) United States Patent
Long et al.

(10) Patent No.: US 9,443,062 B2
(45) Date of Patent: Sep. 13, 2016

(54) SYSTEM AND METHOD FOR DISABLING OR ENABLING AUTOMATED DISPENSERS

(75) Inventors: Avery Dallas Long, Madison, AL (US); Harvey Allen Nix, Birmingham, AL (US); Erin Melisa Snow, Vestavia Hills, AL (US); Sean Michael Kelly, Cookeville, TN (US)

(73) Assignee: Proventix Systems, Inc., Birmingham, AL (US)

( * ) Notice: Subject to any disclaimer, the term of this patent is extended or adjusted under 35 U.S.C. 154(b) by 0 days.

(21) Appl. No.: 13/432,897

(22) Filed: Mar. 28, 2012

(65) Prior Publication Data

US 2013/0261795 A1    Oct. 3, 2013

(51) Int. Cl.
*G06F 17/00* (2006.01)
*G06F 19/00* (2011.01)
*G08B 21/24* (2006.01)

(52) U.S. Cl.
CPC ......... *G06F 19/3462* (2013.01); *G08B 21/245* (2013.01); *G06F 19/327* (2013.01)

(58) Field of Classification Search
CPC .................................................. G08B 21/245
USPC ........................................................ 700/241
See application file for complete search history.

(56) References Cited

U.S. PATENT DOCUMENTS

| | | | | |
|---|---|---|---|---|
| 5,199,118 A * | 4/1993 | Cole | ........................ | A47K 1/04 4/619 |
| 5,610,589 A * | 3/1997 | Evans | .................. | G08B 21/245 340/573.1 |
| 5,966,753 A * | 10/1999 | Gauthier et al. | .................. | 4/623 |
| 6,189,163 B1 * | 2/2001 | Van Marcke | ..................... | 4/623 |
| 6,577,240 B2 * | 6/2003 | Armstrong | ................. | 340/573.1 |
| 6,876,902 B2 * | 4/2005 | Nikolich | ..................... | 700/242 |
| 7,009,519 B2 | 3/2006 | Leonard et al. | | |
| 7,155,306 B2 * | 12/2006 | Haitin et al. | .................. | 700/242 |
| 7,551,092 B1 | 6/2009 | Henry | | |
| 7,565,301 B2 * | 7/2009 | Moubayed | ............ | G06F 19/326 367/76 |
| 7,597,122 B1 | 10/2009 | Smith | | |
| 7,617,850 B1 | 11/2009 | Dorney | | |
| 7,659,824 B2 | 2/2010 | Prodanovich et al. | | |
| 7,783,380 B2 * | 8/2010 | York et al. | ..................... | 700/240 |
| 7,898,407 B2 * | 3/2011 | Hufton et al. | ........... | 340/539.11 |
| 8,085,155 B2 * | 12/2011 | Prodanovich et al. | .... | 340/573.1 |
| 8,178,042 B2 * | 5/2012 | Jung et al. | ....................... | 422/62 |
| 8,237,558 B2 * | 8/2012 | Seyed Momen et al. | ........................ | 340/539.11 |
| 8,294,584 B2 * | 10/2012 | Plost | .......................... | 340/573.1 |
| 8,350,706 B2 * | 1/2013 | Wegelin et al. | ........... | 340/573.1 |
| 8,368,544 B2 * | 2/2013 | Wildman et al. | .......... | 340/573.1 |
| 8,371,501 B1 * | 2/2013 | Hopkins | ....................... | 235/380 |
| 8,400,309 B2 * | 3/2013 | Glenn et al. | ............... | 340/573.1 |
| 8,400,310 B2 * | 3/2013 | Brow | ......................... | 340/573.1 |

(Continued)

*Primary Examiner* — Michael K Collins
(74) *Attorney, Agent, or Firm* — Paul Sykes; Nicholas J. Landau; Bradley Arant Boult Cummings LLP

(57) ABSTRACT

A system and method for disabling or enabling automated dispensers based upon data received by a server or a control unit. In one embodiment, the system disables automated dispensers in a room of a medical facility based upon health condition data of a patient resident in the room. In another embodiment, the system enables automated dispensers upon receipt of data identifying user types authorized to use the dispenser that are associated with wearable tags in proximity to the dispensers. In still another embodiment, the system controls the order in which automated dispensers are enabled in order to facilitate compliance with workflow procedures for a facility.

8 Claims, 6 Drawing Sheets

(56) References Cited

U.S. PATENT DOCUMENTS

| | | |
|---|---|---|
| 8,502,680 B2 * | 8/2013 | Tokhtuev et al. .......... 340/573.1 |
| 8,639,527 B2 * | 1/2014 | Rensvold et al. ................ 705/2 |
| 8,646,656 B2 * | 2/2014 | Johnson ........................ 222/52 |
| 2002/0000449 A1 * | 1/2002 | Armstrong ..................... 222/52 |
| 2008/0100441 A1 * | 5/2008 | Prodanovich et al. .... 340/572.1 |
| 2008/0136649 A1 | 6/2008 | Van De Hey |
| 2009/0037020 A1 * | 2/2009 | Brown .......................... 700/240 |
| 2009/0091458 A1 * | 4/2009 | Deutsch ............... G06F 19/327 340/573.1 |
| 2009/0195385 A1 | 8/2009 | Huang |
| 2009/0224907 A1 * | 9/2009 | Sinha et al. ............. 340/539.11 |
| 2009/0265990 A1 * | 10/2009 | Stratmann ......................... 49/31 |
| 2009/0267776 A1 * | 10/2009 | Glenn ................. G08B 21/245 340/573.1 |
| 2009/0272405 A1 * | 11/2009 | Barnhill et al. ................ 134/18 |
| 2009/0299787 A1 * | 12/2009 | Barnhill ............................ 705/7 |
| 2010/0125362 A1 | 5/2010 | Canora et al. |
| 2010/0164728 A1 * | 7/2010 | Plost .......................... 340/573.1 |
| 2010/0230435 A1 * | 9/2010 | Wegelin .......................... 222/52 |
| 2010/0315243 A1 * | 12/2010 | Tokhtuev et al. ............. 340/603 |
| 2011/0068930 A1 * | 3/2011 | Wildman et al. .......... 340/573.1 |
| 2011/0088809 A1 | 4/2011 | Lin |
| 2011/0227740 A1 * | 9/2011 | Wohltjen ................... 340/573.1 |
| 2011/0254682 A1 * | 10/2011 | Sigrist Christensen .......... G06F 19/327 340/539.12 |
| 2011/0260827 A1 | 10/2011 | Shapiro et al. |
| 2011/0316703 A1 | 12/2011 | Butler et al. |
| 2011/0320134 A1 | 12/2011 | Butler et al. |
| 2012/0062382 A1 * | 3/2012 | Taneff ................. G08B 21/245 340/573.1 |
| 2012/0212582 A1 * | 8/2012 | Deutsch .......................... 348/46 |
| 2012/0245729 A1 * | 9/2012 | Wegelin et al. ............. 700/231 |
| 2013/0045685 A1 * | 2/2013 | Kiani ........................... 455/41.2 |
| 2013/0127615 A1 * | 5/2013 | Snodgrass ................ 340/539.13 |
| 2014/0200538 A1 * | 7/2014 | Euliano et al. ............... 604/361 |

\* cited by examiner

SYSTEM AND METHOD FOR DISABLING OR ENABLING AUTOMATED DISPENSERS

The present disclosure relates to a system and method for disabling or enabling automated dispensers based upon data received by a server or a control unit.

BACKGROUND

Within the healthcare field, automated hand sanitizer dispensers are placed in rooms and hallways of medical facilities to encourage healthcare workers to perform hand hygiene before and after caring for patients in order to prevent Healthcare-Associated Infections (HAIs). However, there are situations where healthcare workers cannot properly disinfect their hands and prevent HAIs through the use of an automated hand sanitizer dispenser. For example, a healthcare worker caring for a patient afflicted with a health condition known as *Clostridium difficile*, which is more commonly referred to as *C. difficle*, must use soap and water to remove bacterial spores from their skin to avoid transferring the infection to another patient or coworker. Therefore, in order to prevent healthcare workers from using automated hand sanitizer dispensers while caring for patients identified under contact precautions for *C. difficile*, medical facilities have personnel manually remove the hand sanitizer product from dispensers within a predetermined proximity of rooms in which patients are resident. However, as the number of patients affected by *C. difficle* increases, compliance with the current practice proves difficult and burdensome for personnel. Thus, more efficient systems and methods are needed for controlling the use of automated hand sanitizer dispensers at a medical facility based upon health condition data of resident patients.

Further, systems and methods for controlling the use of automated dispensers at a medical facility are needed wherein automated dispensers include but are not limited to automated hand sanitizer dispensers. As an example, automated gloves dispensers are placed in rooms and hallways of medical facilities so that healthcare workers can obtain latex gloves prior to treating a patient. However, since medical facilities lack systems and methods for limiting the use of automated gloves dispensers to healthcare workers, patients and visitors alike can obtain latex gloves. As such, an economic loss occurs each time someone other than a healthcare worker uses an automated gloves dispenser. Thus, systems and methods are needed to control the use of automated dispensers at a medical facility.

Still further, systems and methods are needed for controlling the order in which automated dispensers are used to facilitate compliance with workflow procedures. As an example, a healthcare worker preparing to treat a patient must perform hand hygiene prior to obtaining latex gloves in order to reduce the likelihood of the patient acquiring an HAI. However, medical facilities lack systems and methods for causing healthcare workers to use an automated hand sanitizer dispenser before an automated gloves dispenser. As a result, healthcare workers can obtain latex gloves prior to disinfecting their hands, which increases the likelihood of transferring contaminants from their hands to the latex gloves and ultimately the patient. Thus, systems and methods are needed to control the order in which automated dispensers are used.

SUMMARY

The present disclosure may address one or more of the problems and deficiencies discussed above. However, it is contemplated that the disclosure may prove useful in addressing other problems and deficiencies in a number of technical areas. Therefore, the present disclosure should not necessarily be construed as limited to addressing any of the particular problems or deficiencies discussed herein.

The present disclosure relates to a system for disabling or enabling an automated dispenser with the system comprising a server and a control unit. In one embodiment, the server receives data and based upon data issues a command to the control unit in order to disable or enable the dispenser. The control unit can be configured to disable or enable the dispenser in many different ways. For example, a switching mechanism operable to power gate a power supply for the dispenser can be used. Alternatively, a logic controller configured to disable or enable the dispenser can be used. The control unit also includes a tag reader operable to detect the presence of wearable tags, preferably in the form of a Radio Frequency Identification (RFID) tag, and communicate to the server data specific to the presence, identification, and movement of wearable tags. Therefore, based upon this data, the server can issue a command to the control unit in order to disable or enable the dispenser.

In one embodiment, a server receives health condition data for a patient from a medical facility's database at predetermined intervals and determines from data whether the patient is under contact precautions. If the patient is under contact precautions, then the server issues a command to a control unit to disable automated hand sanitizer dispensers in the patient's room. The automated hand sanitizer dispensers remain disabled until the server receives data indicating the occurrence of at least one of the following events: 1.) patient discharged and patient's room sanitized by hospital personnel; 2.) patient transferred and patient's room sanitized by hospital personnel; or 3.) healthcare worker inputs health condition data to the server confirming patient is no longer under contact precautions. Also, while the automated hand sanitizer dispensers are disabled, a feedback device associated with the control unit displays a message reminding individuals in proximity to the dispensers that the patient is under contact precautions and that soap and water must be used for hand hygiene.

In another embodiment, a server receives data specific to user types of wearable tags in proximity to an automated dispenser and based upon data enables the dispenser. More specifically, the server enables the dispenser whenever data matches a user type authorized to use the dispenser. User types may include, for example, nurse, physician, physician specialty, environmental, and security. Thus, if the server is programmed to enable the dispenser for a nurse, then data identifying a wearable tag with a nurse user type in proximity to the dispenser prompts the server to issue a command to a control unit to enable the dispenser. Further, after a predetermined interval of time, the server issues a command to the control unit to disable the dispenser in order to prevent unauthorized use of the dispenser.

In yet another embodiment, a server controls the order in which automated dispensers are used to facilitate compliance with workflow procedures. For example, issuance of a command to a control unit to enable an automated gloves dispenser for a healthcare worker can be conditioned based upon whether the server received data confirming the healthcare worker's prior use of an automated hand sanitizer dispenser within a predetermined interval of time.

These and other features, aspects, and advantages of the present disclosure will become better understood with reference to the following detailed description, appended claims, and accompanying drawings.

DESCRIPTION

The various embodiments of the present disclosure and their advantages may be understood by referring to FIGS. 1 through 5 of the accompanying drawings. The elements of the drawings are not necessarily to scale, emphasis instead being placed upon illustrating the principles of preferred embodiments of the present disclosure. Throughout the drawings, like numerals are used for like and corresponding parts of the drawings. Further, the embodiments described below are to be considered in all aspects as illustrative only and not restrictive in any manner.

As used herein, it is to be understood that the term "server" broadly refers to any computing device with a processor programmed to perform the functions described herein, and may include without limitation traditional server, desktop or notebook computers, tablets, smart phones or PDAs, and any like device now existing or hereinafter developed. The term "feedback device" broadly refers to any visual, auditory, or tactile device capable of conveying information to a person including a display associated with a control unit. The term "automated dispenser" broadly refers to automated hand sanitizer dispensers, automated soap dispensers, automated gloves dispensers, automated towel dispensers, and other similar devices operable to dispense a medical supply that are known to one of ordinary skill in the art and are presently existing or developed hereafter. The term "contact precautions" broadly refers to those precautions used to prevent the spread of an infectious condition which includes using soap and water for hand hygiene.

Figure 1:
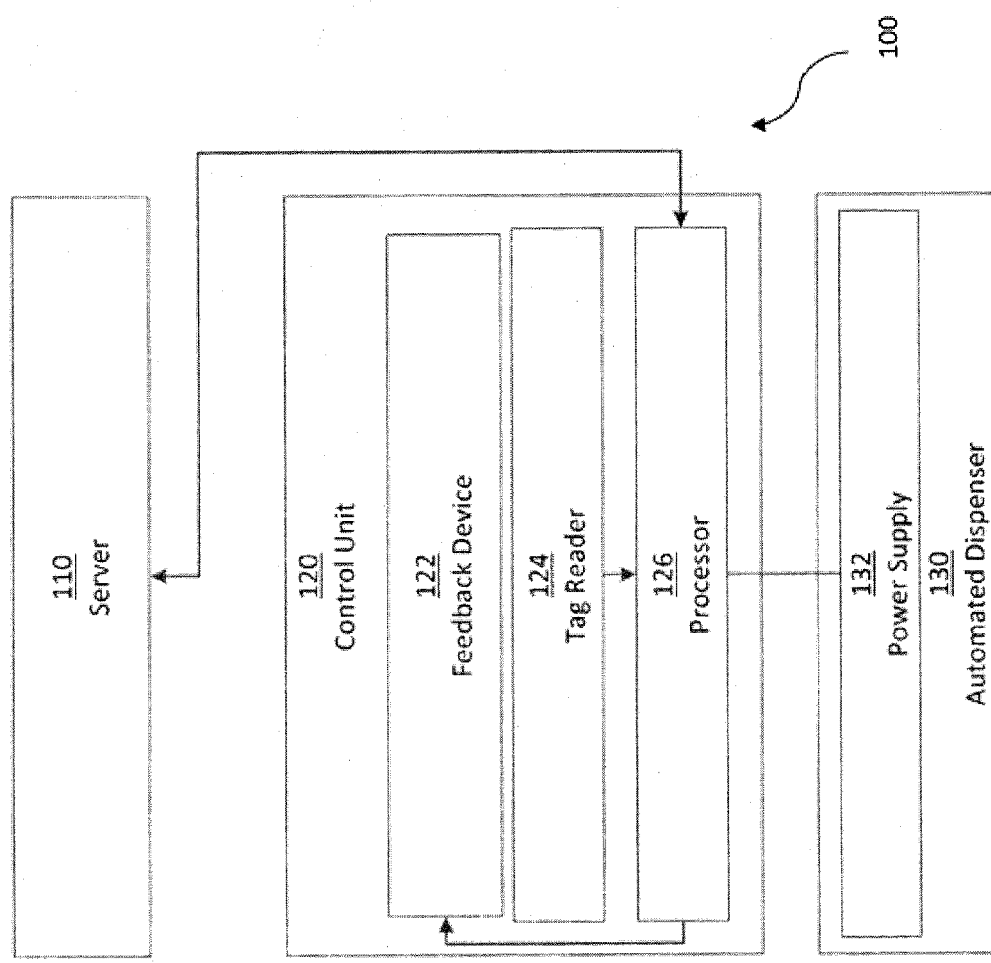
FIG. 1 is a block diagram illustration of an embodiment in accordance with the present disclosure.

As shown in FIG. 1, one embodiment of a system (100) in accordance with the present disclosure includes a server (110) in communication (i.e. wired or wireless) with a control unit (120) operable to disable or enable an automated dispenser (130). The control unit (120) includes a feedback device (122), a tag reader (124), and a processor (126). Also, while FIG. 1 depicts the control unit (120) and the dispenser (130) as separate devices, it is to be understood that the operational and functional characteristics of the control unit (120) can be integrated into the dispenser (130). In this embodiment, the server (110) receives data and based upon data issues a command to the processor (126) to disable or enable the dispenser (130) by way of, for example, controlling a power supply (132) for the dispenser (130). Controlling the power supply (132) may be accomplished in many ways. For example, a switching mechanism (not shown) can be used wherein the switching mechanism gates power to the power supply (132) in response to a signal sent from the processor (126). The switching mechanism may include, for example, electromechanical relays, solid state relays, Bipolar Junction Transistors (BJTs), Field Effect Transistors (FETs), or other similar switching mechanisms known to one of ordinary skill in the art that are presently existing or developed hereafter.

Figure 1A:
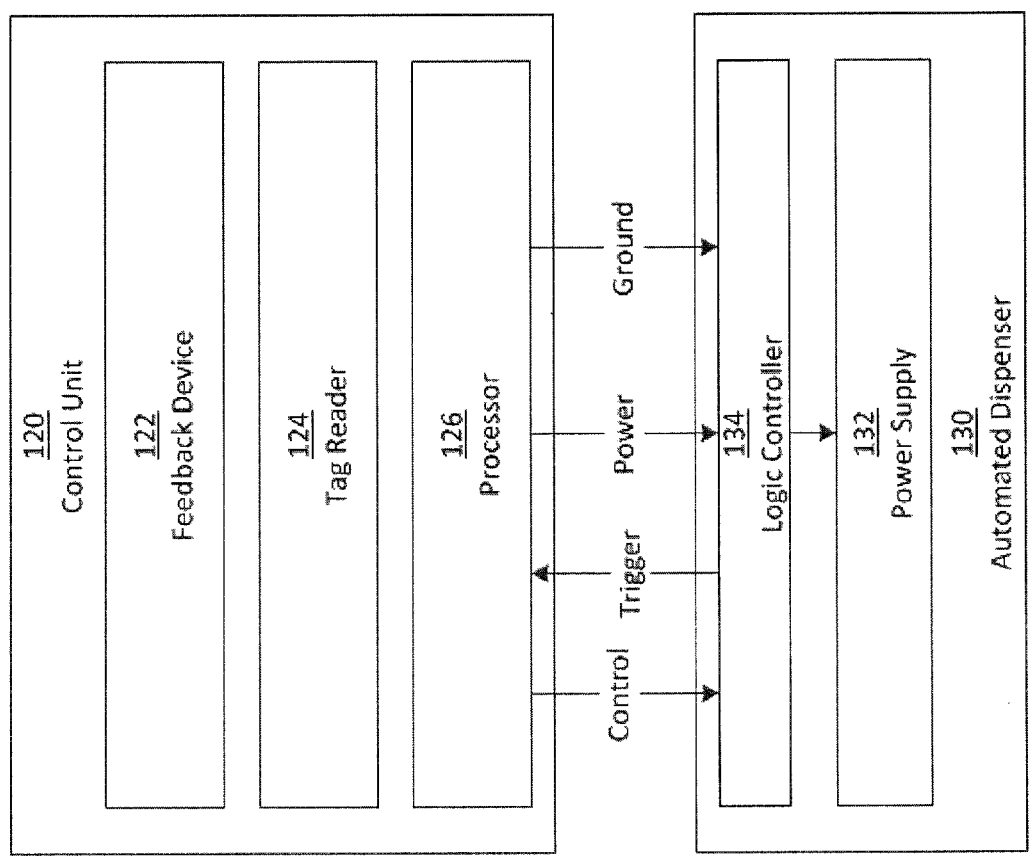
FIG. 1A is a block diagram illustration of another embodiment in accordance with the present disclosure.

Alternatively, a logical interface can be used to disable or enable the dispenser (130). For example, as shown in FIG. 1A, a logic controller (134) associated with the dispenser (130) and in communication (i.e. wired or wireless) with the processor (126) can disable or enable the dispenser (130) in response to a command issued by the processor (126). In this embodiment, the processor (126) issues a command to the controller (134) through a control line. Also, the processor (126) distributes power to the controller (134) through a power line. As such, when the processor (126) issues a command to enable the dispenser (130), the controller (134) distributes power from the power line to the power supply (132). Conversely, when the processor (126) issues a command to disable the dispenser (130), the controller (134) prevents distribution of power to the power supply (132).

Figure 2:
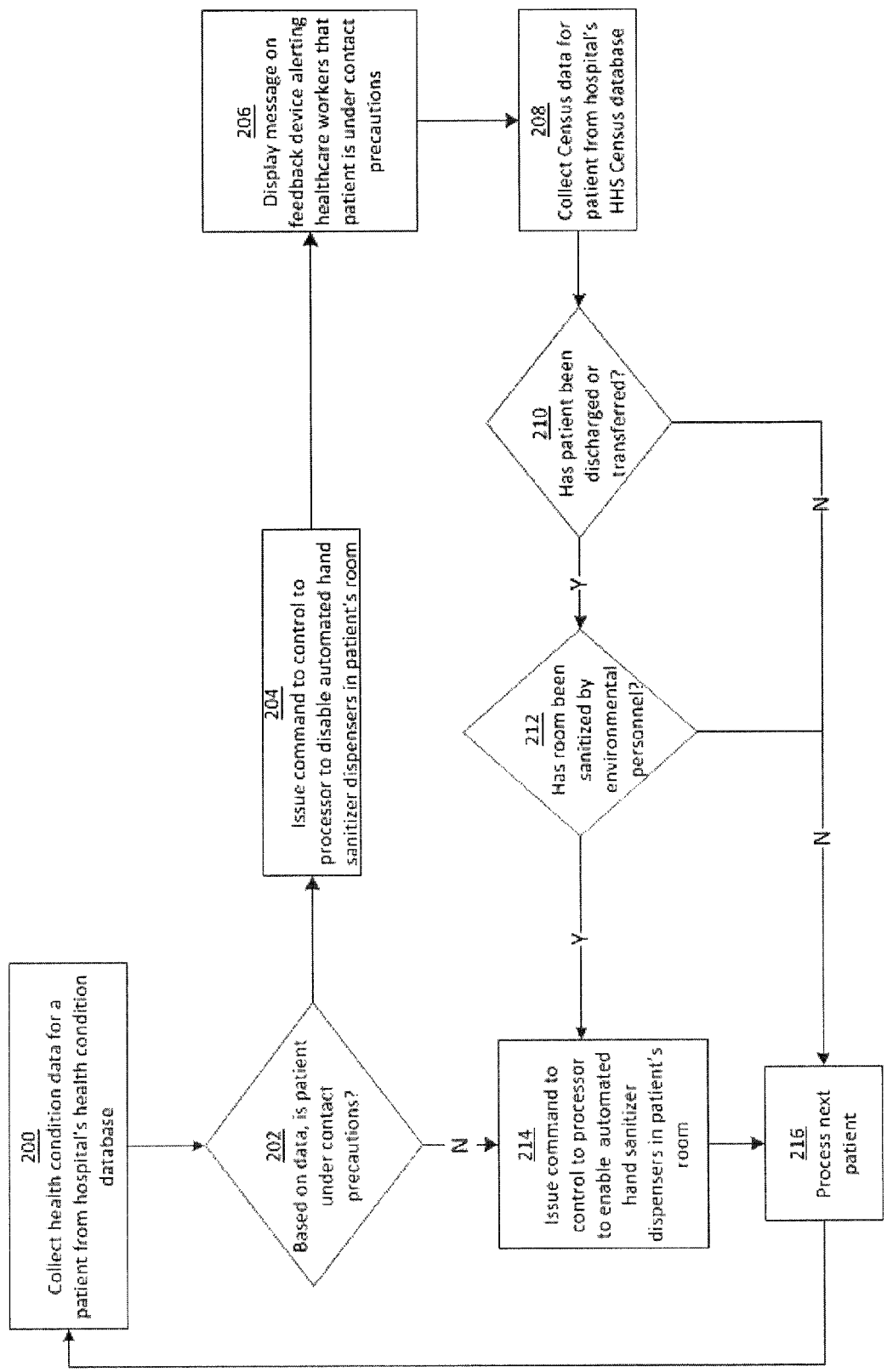
FIG. 2 is a logic flow diagram illustrating one embodiment of a process for disabling or enabling an automated dispenser in response to data received by a server.

Referring now to FIG. 2 in conjunction with FIG. 1, a logic flow diagram is provided depicting one embodiment of processes the system (100) performs in order to disable and re-enable an automated dispenser (130) in a room of a medical facility based upon health condition data of a patient resident in the room. At step (200), the server (110) receives health condition data for the patient from the medical facility's health condition database. Health condition data can also be uploaded to the server (110) by a healthcare worker via the feedback device (122) or similar computing device in communication with the server (110). At step (202), the server (110) determines from health condition data whether the patient is under contact precautions. If the patient is under contact precautions, then step (204) is initiated. At step (204), the server (110) issues a command to the processor (126) to disable the dispenser (130). At step (206), the feedback device (122) displays a message reminding individuals in proximity to the dispenser (130) that the patient is under contact precautions and that soap and water must be used for hand hygiene. Next, at step (208), the server (110) receives census data specific to the patient from hospital's HHS Census database and continues to receive census data at predetermined intervals until step (210). Also, step (212) requires the server (100) receive data indicating the room has been sanitized. In this embodiment, the tag reader (124) monitors entry/exit of tagged personnel and assets into and out of the room. Thus, the tag reader (124) is operable to detect and communicate the presence of tagged environmental personnel and cleaning equipment in the room to the server (110) via the processor (126). Alternatively, environmental personnel can input data to the server (110) confirming sanitization of the room via the feedback device (122). Once step (210) and step (212) are satisfied, step (214) follows as the server (110) issues a command to the processor (126) to enable the dispenser (130).

Figure 3:
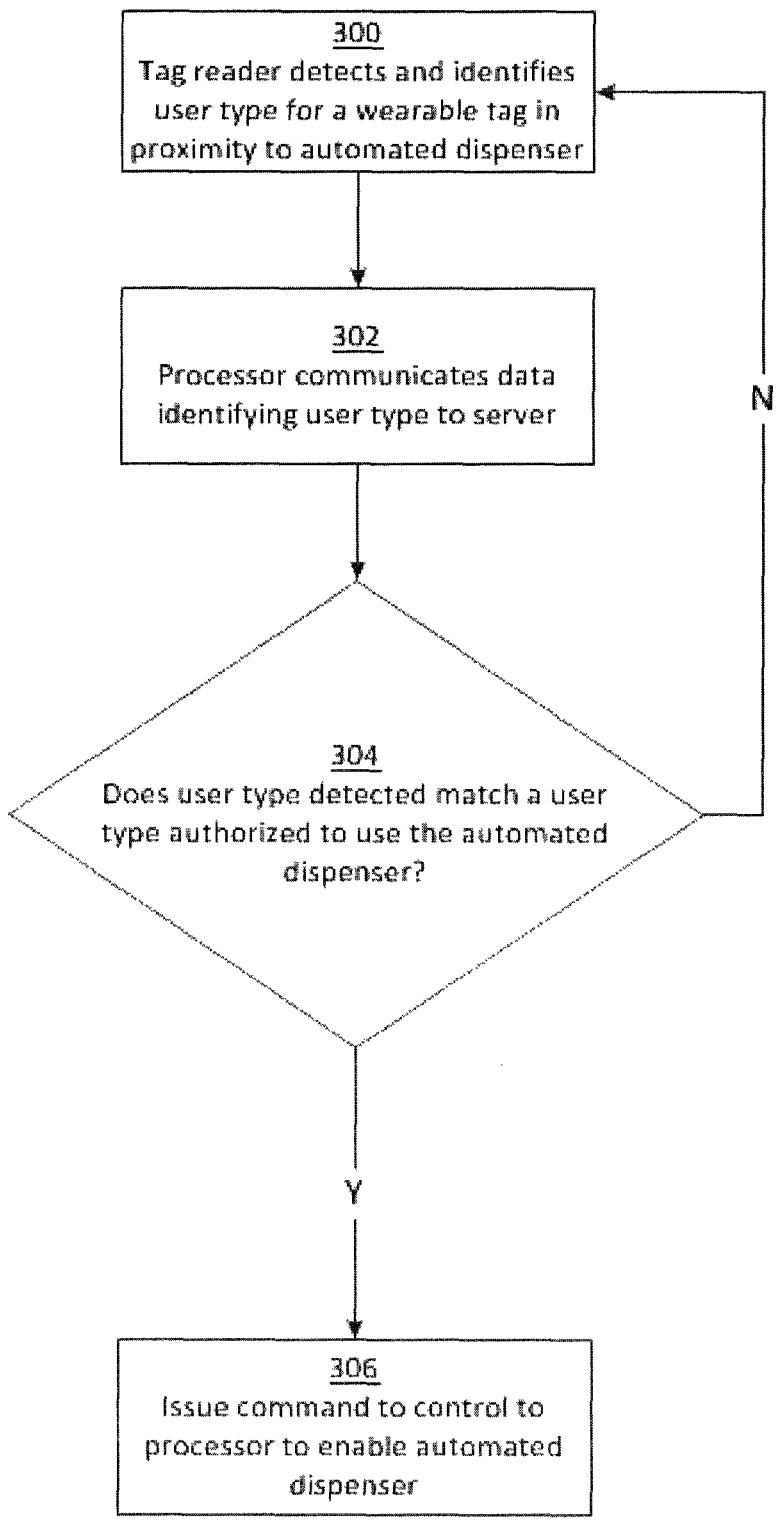
FIG. 3 is a logic flow diagram illustrating another embodiment of a process for enabling an automated dispenser in response to data received by a server or a control unit.

Referring to FIG. 3 in conjunction with FIG. 1, a logic flow diagram is provided depicting one embodiment of processes the system (100) performs in order to control use of the dispenser (130). At step (300), the tag reader (124) detects and identifies a user type (i.e. nurse, physician, visitor, patient, environmental personnel, security personnel, medical supplies, or medical equipment) associated with a wearable tag in proximity to the dispenser (130). Next, at step (302), the processor (126) communicates data identifying the user type to the server (110). Then, upon receiving data, step (304) follows as the server (110) executes a decision-based algorithm in order to determine whether the user type detected matches a user type authorized to use the dispenser (130). If a match exists, step (306) follows and the server (110) issues a command to the processor (126) to enable the dispenser (130). Throughout the discussion of this embodiment of processes, the decision-based algorithm is executed by the server (100); however, it is to be understood that the control unit (120) is operable to store and execute the algorithm through the processor (126).

Figure 4:
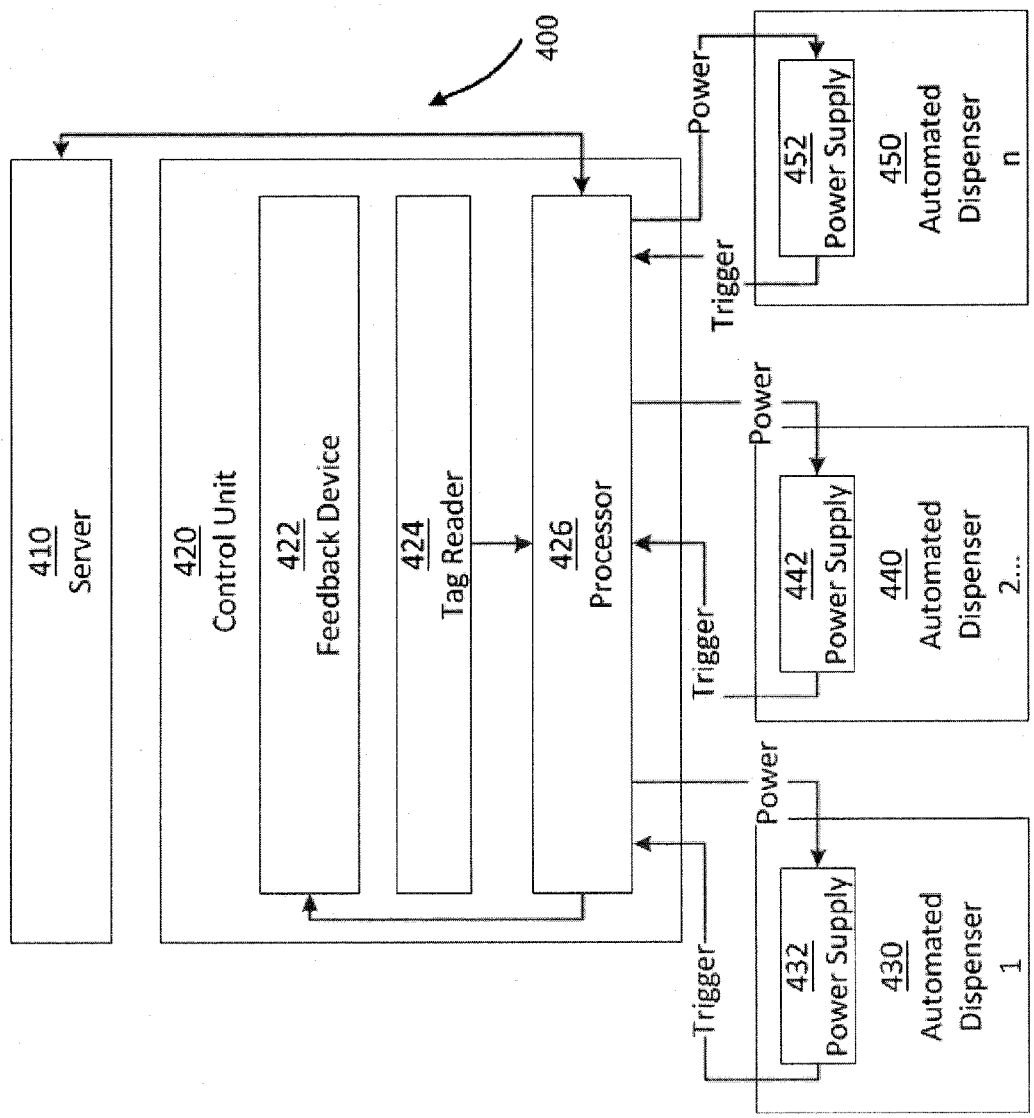
FIG. 4 is a block diagram illustration of yet another embodiment of a system in accordance with the present disclosure.

Referring to FIG. 4, an embodiment of a system (400) in accordance with the present disclosure includes a server (410) in communication (i.e. wired or wireless) with a control unit (420) operable to disable or enable a plurality of automated dispensers, shown generally as (430), (440), and (450). The control unit (420) includes a feedback device (422), a tag reader (424), and a processor (426). In this embodiment, the processor (426) disables or enables at least one of the dispensers in response to a command issued by the server (410). The processor (426) can disable or enable the dispenser in many ways. For example, a switching mechanism (not shown) can be used wherein the switching mechanism is operable to gate power to a power supply for each of the dispensers, shown generally as (432), (442), and (452). Alternatively, the processor (426) can communicate with a logic controller (not shown) associated with each of the dispensers and issue commands to the controller through a control line in order to disable or enable the dispensers. Also, in addition to disabling or enabling the dispensers, the processor (426) is operable to detect use of the dispensers through a trigger line. The trigger line communicates with the power supply and sends a signal to the processor (426) each time the power supply provides power to a load (i.e. a motor) on the dispensers. In response to the signal, the processor (426) communicates the use of one of the dispensers to the server (410).

Figure 5:
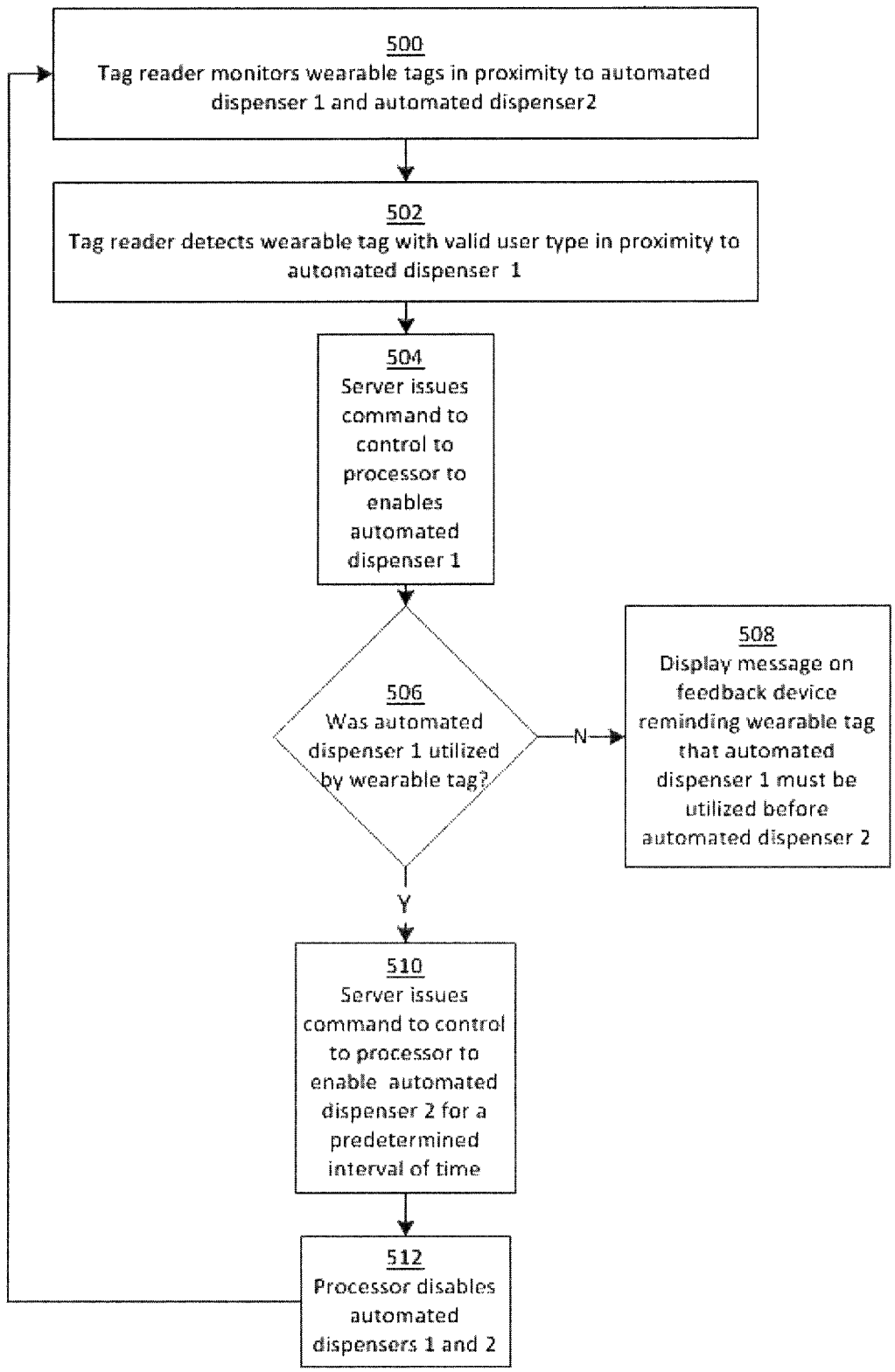
FIG. 5 is a logic flow diagram illustrating an embodiment of a process for using the system of FIG. 4 to facilitate compliance with workflow procedures.

Turning now to FIG. 5 in conjunction with FIG. 4, a logic flow diagram is provided depicting one embodiment of processes the system (400) performs in order to facilitate compliance with workflow procedures specific to the order in which automated dispensers are used. At step (500), the tag reader (424) monitors wearable tags in proximity to automated dispenser 1 (430) and automated dispenser 2 (440). At step (502), the tag reader (426) detects a wearable tag with a valid user type in proximity to automated dispenser 1 (430). At step (504), the server (410) issues a command to the processor (426) to enable automated dispenser 1 (430). Next, at step (506), the server (410) determines whether the wearable tag utilized automated dispenser 1 (430). If automated dispenser 1 (430) has not be used by the wearable tag, then the processor (426) displays a message on the feedback device (422) reminding the wearable tag to use automated dispenser 1 (430). Conversely, if automated dispenser 1 (430) has been used by the wearable tag, then the processor (426) enables automated dispenser 2 (440) for a predetermined interval of time. After the predetermined interval of time has expired, step (512) follows as the processor (426) disables automated dispenser 1 (430) and automated dispenser 2 (440).

While an assortment of embodiments have been disclosed for purposes of illustration, it is obvious that many modifications and variations could be made thereto. Accordingly, the present disclosure is intended to cover all those modifications and variations which fall within the scope of the present disclosure and the appended claims.

What is claimed is:

1. A system comprising:
    a server in communication with a control unit operable to disable or enable an automated dispenser of hand hygiene products, said dispenser located in a room in which a patient at a medical facility is resident or within a predetermined proximity of said room, said server issuing a command to said control unit to disable dispensing of hand hygiene products from said dispenser in response to health condition data that indicates said patient is under contact precautions; and
    a feedback device of said control unit, said feedback device operable to display a message that said patient is under contact precautions while said dispenser is disabled.

2. The system of claim 1, wherein said message directs individuals to use soap and water for hand hygiene.

3. The system of claim 1, wherein said dispenser remains disabled until at least one of the following occurs:
    (a) said server confirms said patient has been discharged or transferred from said medical facility; and
    (b) said server confirms said room has been sanitized by environmental personnel; or
    (c) said server confirms said patient is no longer under contact precautions.

4. The system of claim 1, wherein a tag reader of said control unit detects a wearable tag that is within a predetermined proximity of said dispenser while said dispenser is disabled.

5. The system of claim 4, wherein the tag reader, upon detecting the wearable tag, identifies a user type assigned to the wearable tag.

6. The system of claim 1, wherein said control unit is operable disable or enable said dispenser by controlling a power supply for said dispenser.

7. The system of claim 1, wherein said control unit is operable to disable or enable said dispenser by issuing a command to a logic controller inside said dispenser.

8. A hand hygiene dispensing system comprising:
    a server in communication with a database of a medical facility, the server operable to receive health condition data from the database that is specific to patients resident at the medical facility;
    a control unit in communication with the server, the control unit operable to disable or enable dispensing of hand sanitizer product from an automated hand sanitizer dispenser associated with the control unit in response to commands received from the server based on health condition data, wherein the control unit and the automated hand sanitizer dispenser are located in a room in which a patient is resident; and
    a feedback device of said control unit, the feedback device operable to display a message to use soap and water for hand hygiene while the dispenser is disabled.

* * * * *